(12) United States Patent
Kern et al.

(10) Patent No.: US 8,932,806 B1
(45) Date of Patent: Jan. 13, 2015

(54) METHOD FOR IDENTIFYING T-CELL STIMULATING PROTEIN FRAGMENTS

(76) Inventors: Florian Kern, Berlin (DE); Hans-Dieter Volk, Berlin (DE); Peter Walden, Berlin (DE); Alexander Scheffold, Berline (DE); Rainer Blasczyk, Burgwedel (DE)

( * ) Notice: Subject to any disclaimer, the term of this patent is extended or adjusted under 35 U.S.C. 154(b) by 0 days.

(21) Appl. No.: 09/600,564

(22) PCT Filed: Jan. 15, 1999

(86) PCT No.: PCT/DE99/00175
§ 371 (c)(1),
(2), (4) Date: Nov. 7, 2000

(87) PCT Pub. No.: WO99/36568
PCT Pub. Date: Jul. 22, 1999

(30) Foreign Application Priority Data

Jan. 19, 1998 (DE) ................................. 198 02 174
Jul. 28, 1998 (DE) ................................. 198 34 932

(51) Int. Cl.
*C12Q 1/00* (2006.01)
*A61K 45/00* (2006.01)
*A01N 63/00* (2006.01)

(52) U.S. Cl.
USPC ....... 435/4; 424/85.11; 424/93.71; 424/154.1

(58) Field of Classification Search
USPC .................... 435/7.1, 7.2, 7.21, 7.33
See application file for complete search history.

(56) References Cited

PUBLICATIONS

Woitas et al. "CD 30 Induction and Cytokine profile in Hepatitis C Virus", Journal of Immunology of Immunology, vol. 159, No. 2, pp. 1012-1018, 1997.*
Yanagisawa et al. (International Immunology, 1997, vol. 9 No. 2, pp. 227-237).*

* cited by examiner

*Primary Examiner* — Rodney P Swartz
(74) *Attorney, Agent, or Firm* — Norris McLaughlin & Marcus, P.A.

(57) ABSTRACT

The invention relates to a method for identifying T-cell stimulating protein fragments using the following steps: a) detecting the amino acid sequence of an antigen; b) subdividing the found amino acid sequence of the antigen into protein fragments; c) synthesizing at least one protein fragment; d) incubating a suspension containing t-cells with the protein fragments; e) identifying an induced T-cell cytokine or activation marker by flow-through cytometry, and; f) assigning the T-cells, with which T-cell cytokines and/or activation markers were identified, to the protein fragments which were incubated with the T-cells. The corresponding protein fragments/peptides are synthetically produced with the assistance of the detected positive sequence, and said corresponding protein fragments/peptides can be utilized to produce a medicament for immunostimulation.

8 Claims, 2 Drawing Sheets

SEQUENCE LISTING

```
<160> NUMBER OF SEQ ID NOS: 8

<210> SEQ ID NO 1
<211> LENGTH: 15
<212> TYPE: PRT
<213> ORGANISM: Artificial Sequence
<220> FEATURE:
```

```
<223> OTHER INFORMATION: Description of Artificial Sequence: Fragment of
      the pp65 protein of human cytomegalovirus

<400> SEQUENCE: 1

Ala Arg Asn Leu Val Pro Met Val Ala Thr Val Gln Gly Gln Asn
 1               5                  10                  15

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Fragment of
      the pp65 protein of human cytomegalovirus

<400> SEQUENCE: 2

Ala Arg Asn Leu Val Pro Met Val Ala
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Fragment of
      the pp65 protein of human cytomegalovirus

<400> SEQUENCE: 3

Arg Asn Leu Val Pro Met Val Ala Thr
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Fragment of
      the pp65 protein of human cytomegalovirus

<400> SEQUENCE: 4

Asn Leu Val Pro Met Val Ala Thr Val
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Fragment of
      the pp65 protein of human cytomegalovirus

<400> SEQUENCE: 5

Leu Val Pro Met Val Ala Thr Val Gln
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Fragment of
      the pp65 protein of human cytomegalovirus

<400> SEQUENCE: 6

Val Pro Met Val Ala Thr Val Gln Gly
 1               5
```

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Fragment of
      the pp65 protein of human cytomegalovirus

<400> SEQUENCE: 7

Pro Met Val Ala Thr Val Gln Gly Gln
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Fragment of
      the pp65 protein of human cytomegalovirus

<400> SEQUENCE: 8

Met Val Ala Thr Val Gln Gly Gln Asn
 1               5
```

METHOD FOR IDENTIFYING T-CELL STIMULATING PROTEIN FRAGMENTS

Figure 1:
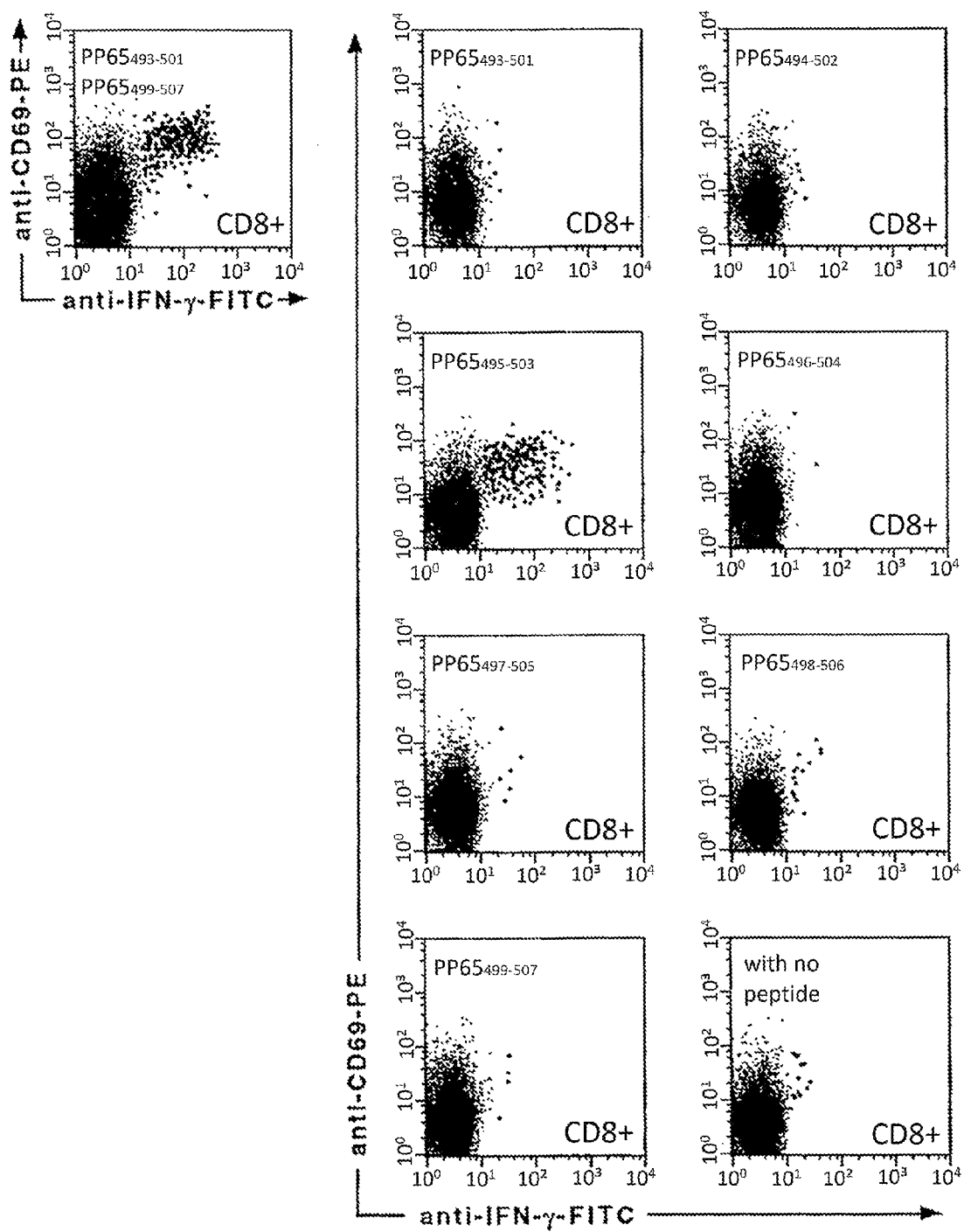

This is a U.S.C. 371 of Application PCT/DE99/00175 filed on Jan. 15, 1999, and claims priority to German applications No. 198 02174.7 filed on Jan. 19, 1998, and 198 34 932.7 filed on Jul. 28, 1998.

The present invention relates to a method for the identification of T-cell stimulating protein fragments by means of T cell induction, a process for the preparation of protein fragments having a sequence which was found by the method according to the invention, and the use of such protein fragments for immune stimulation.

PRIOR ART

The T-cell stimulating protein fragments comprise T cell epitopes which are specifically recognized by T cell receptors and through this recognition stimulate the T cell biosynthesis, inter alia, of cytokines secreted in the usual way.

A known method for the identification of T-cell stimulating protein fragments consists in subdividing a protein the amino acid sequence of which is known into individual overlapping protein fragments. The corresponding synthetically prepared protein fragments are incubated with T cells singly or in groups. After one to three weeks, cell lines or cell clones may be present which could be specifically stimulated by the protein fragment or by at least one of the protein fragments employed. The specificity of these lines or clones can be detected by cytotoxicity tests with appropriate target cells. Due to the experimental design, the stimulated cell lines or cell clones can be assigned to the corresponding T-cell stimulating protein fragments. This method is described in detail in P. Walden et al. (1996), Current Opinion in Immunology, Vol. 8, pp 68-74. Alternatively, the proliferation of cells can be determined after 1 week by the incorporation of $^3$H-thymidine, which method is subject to higher non-specificity, however.

A drawback of these two methods is the high expenditure in terms of apparatus, personnel and time. In addition, it is probable that stimulated T cells die during the long incubation time, e.g., by activation-induced programmed cell death (apoptosis), from which false negative results are obtained.

A method for the flow-cytometric identification of antigen-specific T cells according to S. L. Waldrop et al. (1997), Determination of Antigen-Specific Memory/Effector CD4+ T Cell Frequencies by Flow Cytometry: Evidence for a Novel Antigen-Specific Homeostatic Mechanism in HIV-Associated Immunodeficiency, J. Clin. Invest., Vol. 99, pp 1739-1750, consists in incubating proteins as antigens with peripheral blood mononuclear cells (PBMC). These proteins are processed and presented by antigen-presenting cells. This processing results in protein fragments with which MHC class II molecules are loaded and then arrive at the cellular surface (antigen presentation). The T cells respectively stimulated by the recognition of protein fragments are identified by flow cytometry. It is neither possible to establish the stimulating protein fragments, nor to assign the specifically induced T cells to the inducing protein fragments. The object of this experimental design is mainly to establish whether epitopes presented by MHC class II molecules are present in a protein or a complex antigen, or whether an individual possesses specific MHC class II restricted T cells against such epitopes which may be present or are known to be present, and how high the frequency of these cells is (quantification of the antigen-specific T cells). In addition, further properties of the stimulated T cells can be established (surface markers etc.). However, neither the amino acid sequence of existing epitopes nor the frequency of such epitopes can be established.

Problem and Solution

Therefore, it has been the object of the invention to provide a method by which protein fragments the amino acid sequences of which are known can be identified as stimulating protein fragments within a short period of time. The method is to work also for a small number of T cells without T cell lines or cell clones having to be available. Further, among a large number of protein fragments, it should be possible to detect those which stimulate T cells.

This object is achieved by a method for the identification of T-cell stimulating protein fragments comprising the following steps:

a) establishing the amino acid sequence of an antigen which is a protein or a peptide;
b) subdividing the detected amino acid sequence of said antigen into protein fragments;
c) synthesizing at least one protein fragment having a length of from 8 to 30 amino acids, or cleaving the amino acid sequence of said antigen into at least one protein fragment having a length of from 8 to 30 amino acids, wherein said protein fragment is a subsequence of the established amino acid sequence of said antigen;
d) incubating a suspension containing T cells with the protein fragment or fragments in different experimental runs;
e) identifying of
   (i) at least one T cell cytokine which has been induced by the protein fragment or fragments and synthesized in the T cells, wherein the T cell cytokine or cytokines remain within the cell or are bound to the cell membrane; and/or
   (ii) at least one activation marker which has been induced or expression-enhanced by the protein fragment or fragments and which is expressed in the T cells, wherein said activation marker can be present within the cell or expressed on the cellular surface;
   wherein said T cell cytokine or cytokines or activation markers are identified by flow cytometry; and
f) assigning the experimental runs in which T cells have been stimulated and such stimulation has been recognized by the identification of one or more T cell cytokines and/or one or more activation markers, to the amino acid sequence or sequences of said protein fragments which had been incubated with the T cells.

Advantages

The main advantage of this method according to the invention is that a protein segment with a known sequence can be identified as a T-cell stimulating protein fragment within a very short period of time and, as compared with the conventional method, with very little expenditure. The time between the first incubation of T cells and the flow-cytometric evaluation can be six hours. Extremely low numbers of cells may be sufficient. If a number of $1 \times 10^6$ peripheral white blood cells are initially used, a positive response can be unambiguously established even when 0.1% of the initial number of T cells are stimulated T cells. In contrast, the classical method requires a number of cells of about $8 \times 10^6$ peripheral white blood cells per protein fragment or mixture of protein fragments to be able to perform a successful cytotoxicity test subsequently. Thus, the method according to the invention can be employed with high efficiency for the T cell epitope mapping of protein antigens.

Further, mixtures of freshly isolated cellular blood cells or tissue cells can be used. T cell lines or cell clones are not necessary for this method according to the invention. This results in advantages in terms of less time required for incubation and further, very essentially, in terms of the viability of the T cells which are present as a large pool with a high variability within the short incubation time. Selection and proliferation accompanied by the specific elimination of particular T cells do not occur in the method according to the invention due to the short incubation times.

Preferred sources of the T cells to be stimulated are donors who have previously built up an immunological primary response to the antigen. This may have happened, for example, during an infection or during an immunization. The same situation is found in an autoimmune response.

Another advantage is that the MHC type of the donor need not be known. Thus, for example, protein fragments with 9 amino acids from one protein are incubated with the T cells without knowing the MHC type of the blood or cell donor. Nevertheless, the T-cell stimulating protein fragments can be identified. Thus, knowing the MHC type is not necessary for identifying the epitope. In classical tests using cytotoxic T cell lines or T cell clones, the MHC type of the target cell lines must match that of the effector cells.

Establishing target cell lines from donor blood represents an additional expenditure in terms of material and time.

Further, a large number of protein fragments can be incubated at the same time by the method according to the invention. Low cell numbers and the highly sensitive detection of stimulated T cells allow the identification of the T-cell stimulating protein fragments with clear advantages in time.

Since the number of the protein fragments to be examined can be very high due to the fact that little work is necessary, it is not necessary to narrow down possible epitopes by theoretical predictions. The epitopes are found in a purely empirical way, and therefore, even those T cell epitopes can be found which would not be derived from a theoretical prediction.

With this method, T cells which can be specifically stimulated by particular selected protein fragments can be easily identified.

On the one hand, T-cell stimulating protein fragments bind to defined MHC molecules, and on the other hand, they contain amino acid sequences (epitopes) which can undergo binding to the antigen binding region of the T cell receptor (paratope).

An essential feature of the terms protein or peptide is a sequence of at least nine amino acids. It is not important how the sequence was established. Thus, for a new protein, the sequence may be analyzed for the first time, or for a known protein, it may be read from a data base. The only important thing is that the amino acid sequence of the protein fragment has been determined. The subdivision of the protein or peptide sequence may also be made in a number of different ways. Thus, the protein fragments can be derived from one protein stepwise by the variation of one amino acid. Other overlapping schemes are also possible. This is the classical method of protein mapping.

Suspensions containing T cells within the meaning of this application are characterized by containing cells which are capable of presenting MHC-bound peptides. Thus, in addition to the antigen-presenting cells, the presenting cells may also be T cells, for example.

FURTHER EMBODIMENTS

The method according to the invention is advantageous in the identification of T-cell stimulating protein fragments since said identification of at least one T cell cytokine or activation marker is made on an individual cell level. Even extremely small amounts of T cells containing intracellular cytokines or cytokines bound to the cell membrane are sufficient.

In the method according to the invention for the identification of T-cell stimulating protein fragments, it is preferred that said suspensions containing T cells contain cells which present the protein fragment essentially with MHC class I or II molecules (MHC=major histocompatibility complex). In addition to the amino acids serving for anchoring in the cleft of the MHC molecule (binding anchor), particular sequences which are specifically recognized by a T cell receptor (T cell epitopes) must be present for the protein fragment to function as a T cell epitope.

In the method according to the invention for the identification of T-cell stimulating protein fragments, it is preferred that the protein fragment in the class I restricted presentation comprises from 9 to 11 amino acids and the protein fragment in the class II restricted presentation comprises at least 11 amino acids. It is known that protein fragments binding to MHC class I molecules (MHC=major histocompatibility complex) usually have a length of 9 amino acids whereas protein fragments binding to MHC class II molecules are somewhat longer and more variable in length.

It is advantageous that the protein fragments, despite the short incubation time, are sufficiently taken up by the MHC molecules present on the cellular surface to enable an unambiguous identification of stimulated T cells after six hours, for example. Further, if short protein fragments are used (class I with 9 amino acids and class II with preferably 11-15 amino acids), the epitope present in a stimulating amino acid sequence can be narrowed down to a maximum extent.

In the method according to the invention for the identification of T-cell stimulating protein fragments, it is preferred that said suspension containing T cells is a suspension of whole blood, peripheral white blood cells (PWBC), splenocytes, thymocytes, bone marrow, cerebrospinal fluid and/or lymph node cells. The method is considerably simplified by the fact that the suspensions containing T cells may be derived from a wide variety of sources. Further, it is particularly advantageous that processing of the T cells is not required. Thus, the T cells need not be enriched, and removal or destruction of other cells is not necessary. In this way, the method according to the invention can be handled more simply as a routine method. The method is less susceptible to interference from culture conditions, contaminations, selections due to culturing and the selecting of specific clones, as compared to the conventional method. A representative picture of T cells in general and T cells stimulated by protein fragments can be established by this method.

In the method according to the invention for the identification of T-cell stimulating protein fragments, it is preferred that said suspension containing T cells is derived from the patients to be subjected to therapy, from donors or from animals. If the suspension containing T cells is derived from a patient, the identification may be used, for example, to establish against which protein fragment/epitope of a viral antigen a T cell response can be induced. Such a protein fragment/epitope can then be selectively employed for the stimulation of additional T cells in the patient. The thus induced and proliferation-stimulated cells can thus be expanded and subsequently reinfused into the patient.

The method according to the invention can also be used in veterinary medicine. A wide variety of animal species and also constellations of animal patients and donors as a source of the suspension containing T cells can be contemplated.

In the method according to the invention for the identification of T-cell stimulating protein fragments, it is preferred that the antigens, i.e., proteins or peptides, are derived from microorganisms, macroorganisms, cells, cell cultures and/or tissues of donors or patients. Microorganisms include, for example, viruses, bacteria, fungi, monocellular organisms, parasites. Macroorganisms include, for example, all polycellular eukaryotes. This is the very source which is important to influencing allergies. This includes animals and plants. Cells, cell cultures or even whole tissues consisting of one or more strata or cell types can be used.

In the method according to the invention for the identification of T-cell stimulating protein fragments, it is preferred that the T cell cytokines are of the types interferon-γ, TNF-α (tumor necrosis factor-alpha) or interleukin 2. However, other cytokines are also possible. The only precondition is that these cytokines can be fluorescence-labeled.

Activation markers which are expressed or expression-enhanced due to the T cell stimulation by the protein fragments can also be identified. This may be exemplified by the marker CD69. For the identification of activation markers which are present on the cellular surface or which are not secreted, inhibition of secretion may no longer be required.

Cytokines and surface markers are described in detail in Abul K. Abbas et al. (1997), Cellular and Molecular Immunology, Philadelphia, 3rd edition, ISBN 0-7216-4024-9.

In the method according to the invention for the identification of T-cell stimulating protein fragments, it is more preferred that the T cell cytokines remain within the cell after inhibition of secretion. It is important that the stimulation observed can be unambiguously assigned to T cells.

In the method according to the invention for the identification of T-cell stimulating protein fragments, it is preferred that the stimulation is detected by flow cytometry. The essential principle is that markers present within the cell or on its surface, such as cytokines or surface markers, are contacted with a specific detector, for example, an antibody, the detector being loaded with a fluorescent dye. After excitation by laser light of this fluorescent dye on the cells focused in a liquid flow, the flow cytometer records the emitted scattered light and fluorescence signals so that a simultaneous or later analysis of the cells is possible. Such techniques are described in detail in Howard M. Shapiro (1995), Practical Flow Cytometry, New York, 3rd edition, ISBN 0-471-30376-3. The detection of intracellular cytokines is described in L. J. Picker et al. (1995), Blood, Vol. 86, pp 1408.

Preparation of T-Cell Stimulating Protein Fragments

The invention further comprises a process for the preparation of a protein fragment/peptide which is T-cell stimulating and whose amino acid sequence or initial amino acid sequence was found by the method according to the invention for the identification of T-cell stimulating protein fragments, wherein said protein fragment/peptide is prepared by the solid phase method, liquid phase method or by protein biosynthesis in a host.

Solid phase synthesis: Solid phase synthesis is described in detail in Solid Phase Synthesis, E. Atherton and R. C. Sheppard (1989), IRL Press, ISBN 1-85221-133-4, and Amino Acid and Peptide Syntheses, J. Jones, Oxford Science Publication (1992), ISBN 0-19-855668-3.

Liquid phase synthesis: The liquid phase synthesis or solution technique is set forth in Methoden der Organischen Chemie (Houben/Weyl), Vol. 15/Nos. 1 and 2, E. Wunsch (editor), Thieme Verlag Stuttgart, 1974.

In a process for the preparation of a protein fragment/peptide which is T-cell stimulating and whose amino acid sequence or initial amino acid sequence was found by the method according to the invention for the identification of T-cell stimulating protein fragments, wherein said protein fragment/peptide is prepared by the solid phase method, liquid phase method or by protein biosynthesis in a host, it is further advantageous when said protein fragment/peptide contains insertions, deletions or substitutions (modifications) wherein one, two, three or more amino acids have been exchanged, deleted or inserted, wherein said modified protein fragment/peptide has essentially the same function with respect to the stimulation of T cells as the non-modified protein fragment/peptide.

In a process for the preparation of a protein fragment/peptide of the kind as mentioned above, it is particularly advantageous when said protein fragment/peptide contains at least one additional naturally occurring or not naturally occurring amino acid and/or a protecting group at the N-terminal and/or C-terminal end (extended modification), wherein the extendedly modified protein fragment/peptide has essentially the same function with respect to the stimulation of T cells as the non-modified protein fragment/peptide.

Abbreviations: The abbreviations used in the text are defined by the rules established by the IUPAC-IUB Commission for Biochemical Nomenclature (Biochemistry 11: 1726 (1972), and Biochem. J. 219: 345 (1984)). The following usual abbreviations are employed: Ala=A=alanine; Arg=R=arginine; Asn=N=asparagine; Cys=C=cysteine; Gln=Q=glutamine; Glu=E=glutamic acid; Gly=G=glycine; His=H=histidine; Ile=I=isoleucine; Leu=L=leucine; Lys=K=lysine; Met=M=methionine; Phe=F=phenylalanine; Pro=P=proline; Ser=S=serine; Thr=T=threonine; Trp=W=tryptophan; Tyr=Y=tyrosine; and Val=V=valine.

It is advantageous if the protein fragments presented in a state bound to MHC class II molecules hay amino protecting groups or carboxy protecting groups or their variants, depending on the type of terminus.

The protecting group or its variants for the N terminus can be alkyl, aryl, alkylaryl, aralkyl, alkylcarbonyl or arylcarbonyl groups having from 1 to 10 carbon atoms, preferably naphthoyl, naphthylacetyl, naphthylpropionyl, benzoyl groups, or an acyl group having from 1 to 7 carbon atoms.

The protecting group or its variants for the C terminus can be an alkoxy or aryloxy group having from 1 to 10 carbon atoms, or an amino group.

Use of T-Cell Stimulating Protein Fragments as a Medicament

Particularly preferred is the use of a protein fragment/peptide whose amino acid sequence or initial amino acid sequence was found by the method according to the invention for the identification of T-cell stimulating protein fragments and which was produced by the preparation process according to the invention, for the preparation of a medicament for immune stimulation.

In said use of a protein fragment/peptide, it is more preferred that said immune stimulation is a vaccination or desensitization.

In said vaccination, the sequence of proteins from viruses, bacteria, monocellular or polycellular eukaryotes as antigens is established and then subdivided into protein fragments which are added to suspensions containing T cells according to the invention. The positive samples in which a T-cell stimulating protein fragment is present are used as a starting point for the preparation of a vaccine.

In said desensitization, protein fragments/peptides are established which trigger the undesired immunological response. Then, the T-cell stimulating protein fragments/peptides or the medicaments prepared th r from according to the preparation method are administered to the patient. The respectively desired effect (stimulation or desensitization) is achieved or enhanced through the kind and site of the application and the dosage (e.g., high-dose or low-dose tolerance induction) and the accompanying administration of, for example, stimulating or tolerifying cytokines or similar medicaments having immunomodulatory activity. Protein fragments which were not found by this method according to the invention have already been successfully employed as medicaments, e.g., in the vaccination of bovines against foot-and-mouth disease (Collen et al., J. Immunol. 1991; 146: 749-755). The peptide identified in our Example was independently found by another group using conventional technology and is being tested as a vaccine (Diamond et al., Blood 1997; 5: 1751-1767).

EXAMPLES

Example 1

See FIG. 1/2

Mononuclear cells were prepared from the peripheral blood, obtained by venous punction, of an HLA-typed female patient possessing the MHC class I allele HLA-A*0201. The patient additionally possessed antibodies against human cytomegalovirus. The cells prepared by a standard method were incubated with the peptides stated below for six hours under optimized conditions. These peptides are fragments of a protein fragment, known from the literature, of the pp65 protein of human cytomegalovirus (Swiss-Prot PO6725) having a length of 15 amino acids (Ala Arg Asn Leu Val Pro Met Val Ala Thr Val Gln Gly Gln Asn, $pp65_{493-507}$). This protein fragment is known to be capable of inducing HLA-A2 restricted cytotoxic T cells in a bulk culture, i.e., to contain a T-cell epitope presented with HLA-A2 (M. R. Wills et al. (1996), J. Virol. Vol. 70, pp 7569-5779). The length of 9 amino acids for the fragments to be tested was chosen because this is the typical length of epitopes presented with MHC class I molecules (H. G. Rammensee et al. (1995), Immunogenetics, Vol. 41, pp 178-228). The peptides used respectively overlap by 8 amino acids, for successive peptides, and thus comprise all possible fragments of this length. The peptides were employed as a mixture of all peptides or singly. The peptide concentration in the Example shown was 1 µg/ml for each peptide.

The following peptides were employed:
1) Ala Arg Asn Leu Val Pro Met Val Ala [SEQ ID NO.:2]
2) Arg Asn Leu Val Pro Met Val Ala Thr [SEQ ID NO.:3]
3) Asn Leu Val Pro Met Val Ala Thr Val [SEQ ID NO.:4]
4) Leu Val Pro Met Val Ala Thr Val Gln [SEQ ID NO.:5]
5) Val Pro Met Val Ala Thr Val Gln Gly [SEQ ID NO.:6]
6) Pro Met Val Ala Thr Val Gln Gly Gln [SEQ ID NO.:7]
7) Met Val Ala Thr Val Gln Gly Gln Asn [SEQ ID NO.:8]

Incubations with the mixture of all peptides (Figure: upper left diagram) and with peptide 3 alone (Figure: middle column, second diagram from above) resulted in the production of IFN-γ in T cells, detected by measurement in a flow cytometer on the individual cell level (J. L. Picker et al. (1995), Blood, Vol. 86, pp 1408-1419). None of the other individually tested peptides had this effect. A study published in the literature identified exactly the same epitope within the same protein segment by conventional methods and clearly confirms our result (D. J. Diamond et al. (1997), Blood, Vol. 90, pp 1751-1767).

Legend for FIG. 1/2:

Detection of intracellular interferon-γ in CD8+ T lymphocytes after stimulation with a mixture of the 7 peptides stated (upper row, leftmost diagram) or the individual peptides, $pp65_{493-501}$, to $pp65_{499-507}$. The marker CD69 was used as an activation marker. The representation is limited to CD3+/CD8+ events, and the average fluorescence intensity is stated.

Example 2

Figure 2:
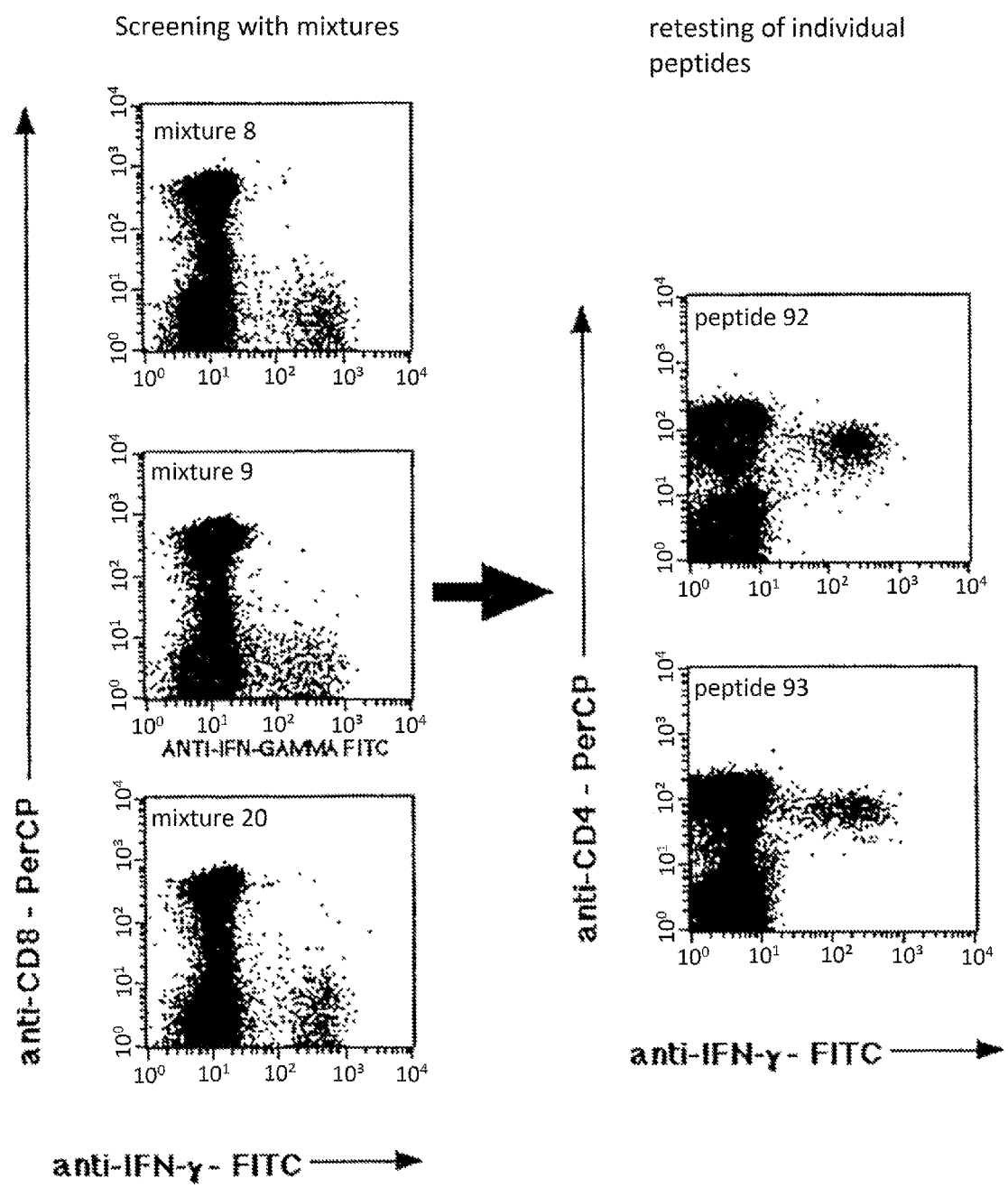

See FIG. 2

Mononuclear cells were prepared from the peripheral blood, obtained by venous punction, of an HLA-typed female patient possessing the MHC class II allele HLA-DR11. The patient additionally possessed antibodies against human cytomegalovirus. The cells prepared by a standard method were incubated with mixtures of 11 or 12 peptides each having a length of 15 amino acids with 11 overlaps respectively, corresponding to the sequence of the pp65 matrix phosphoprotein (Swiss-Prot PO6725), for six hours under optimized conditions (a total of 138 peptides). [SEQ ID NO.:1] The peptide concentration was 1 µg/ml for each peptide. Three out of a total of 24 mixtures clearly stimulated CD4+ T cells. Due to the experimental design (occurrence of particular peptides in particular mixtures), 2 peptides could thus be clearly identified which were responsible for the stimulation. This result was confirmed by the stimulation with the respective individual peptides under otherwise equal conditions. The identified peptides were the neighboring peptides $pp65_{365-379}$ and $pp65_{369-383}$. These sequences are largely congruent with the following HLA-DR11-presented peptide sequences described in the literature, which were identified as T-cell stimulating sequences in the conventional way: $pp65_{361-376}$ and $pp65_{369-384}$ (Khattab et al. (1998), Journal of Medical Virology, Vol. 52, pp 68-76), i.e., the stimulating peptides are found within the segment defined by the amino acids 361 and 384. A further narrowing down of the epitope sequence to the postulated length of 11 amino acids has not been done.

Legend for FIG. 2/2:

Detection of intracellular interferon-γ in CD3+/CD8− T lymphocytes (left) after stimulation with the peptide mixtures 8, 9 and 20, or in CD3+/CD4+ T lymphocytes (right) after stimulation with the individual peptides $pp65_{365-379}$ and $pp65_{369-383}$. In the screening (right), peptide mixtures were used, and CD3 and CD8 were used as T cell markers. Since the INF-γ+ populations on the left side are CD3+/CD8−, the marker CD4 was used for retesting. The stimulated T cells are clearly CD4+. Only CD3+ cells are shown, and the average fluorescence intensity is stated.

The invention claimed is:

1. A method for the identification of T-cell stimulating protein fragments comprising the following steps:
   a) establishing the amino acid sequence of an antigen which is a protein or a peptide;
   b) synthesizing at least one protein fragment having a length of from 8 to 30 amino acids, or cleaving said antigen to yield at least one protein fragment having a length of from 8 to 30 amino acids, wherein said protein fragment has an amino acid sequence which is a subsequence of the established amino acid sequence of said antigen;
   c) incubating a suspension containing T cells with the protein fragment or fragments in different experimental runs for an incubation time, the incubation time being sufficiently long that the protein fragment or fragments are sufficiently taken up by the major histocompatibility antigen (MHC) molecules present on the cellular surface, said protein fragment or fragments being sufficiently taken up by the MHC molecules when an unambiguous identification of stimulated T cells is possible, and the incubation time being sufficiently short that selection and proliferation of stimulated T-cells do not occur;
   d) identifying
      (i) at least one T cell cytokine which has been induced by the protein fragment or fragments and synthesized in the T cells, wherein the T cell cytokine or cytokines remain within the cell or are bound to the cell membrane; and/or
      (ii) at least one activation marker is expressed or the expression of the marker is increased due to the T cell stimulation by the protein fragment or fragments wherein said activation marker can be present within the cell or expressed on the cellular surface;
   wherein said T cell cytokine or cytokines or activation markers are identified by flow cytometry; and
   e) assigning the experimental runs in which T cells have been stimulated and such stimulation has been recognized by the identification of one or more T cell cytokines and/or one or more activation markers, to the amino acid sequence or sequences of said protein fragments which had been incubated with the T cells.

2. The method for the identification of T-cell stimulating protein fragments according to claim 1, wherein said identification of at least one T cell cytokine or activation marker is made on the individual cell level.

3. The method for identification of T-cell stimulating protein fragments according to claim 1, wherein the suspension of step c) comprises cells which present the protein fragment bound to MHC class I or class II molecules.

4. The method for the identification of T-cell stimulating protein fragments according to claim 3, wherein the protein fragment bound to MHC class I molecules comprises from 9 to 11 amino acids, and the protein fragment bound to MHC class II molecules comprises at least 11 amino acids.

5. The method for the identification of T-cell stimulating protein fragments according to claim 1, wherein said suspension containing T cells is a suspension of whole blood, peripheral white blood cells (PWBC), splenocytes, thymocytes, bone marrow, cerebrospinal fluid and/or lymph node cells.

6. The method for identification of T-cell stimulating protein fragments according to claim 1, wherein said suspension containing T cells is obtained from patients to be subjected to therapy, from donors or from animals.

7. The method for the identification of T-cell stimulating protein fragments according to claim 1, wherein the protein or peptide antigens are obtained from multicellular eukaryotes, cells and/or tissues thereof, and cell cultures and/or tissues of donors or patients.

8. The method for the identification of T-cell stimulating protein fragments according to claim 1, wherein the T cell cytokines are of the types interferon-γ, tumor necrosis factor-α (TNF-α) or interleukin 2.

* * * * *

UNITED STATES PATENT AND TRADEMARK OFFICE
CERTIFICATE OF CORRECTION

| | | |
|---|---|---|
| PATENT NO. | : 8,932,806 B1 | Page 1 of 1 |
| APPLICATION NO. | : 09/600564 | |
| DATED | : January 13, 2015 | |
| INVENTOR(S) | : Kern et al. | |

It is certified that error appears in the above-identified patent and that said Letters Patent is hereby corrected as shown below:

Specification

Column 6, line 33, "hay" -- should read -- have --.

Column 6, line 65, "th r from" -- should read -- therefrom --.

Signed and Sealed this
Eighth Day of December, 2015

Michelle K. Lee
*Director of the United States Patent and Trademark Office*